US010933095B2

(12) United States Patent
Lundquist et al.

(10) Patent No.: US 10,933,095 B2
(45) Date of Patent: Mar. 2, 2021

(54) MULTILAYERED BLOOD PRODUCT (71) Applicant: Reapplix ApS, Birkerod (DK)

(72) Inventors: Rasmus Lundquist, Bronshoj (DK); Niels Erik Holm, Birkerod (DK)

(73) Assignee: Reapplix APS, Birkeroed (DK)

( * ) Notice: Subject to any disclaimer, the term of this patent is extended or adjusted under 35 U.S.C. 154(b) by 572 days.

(21) Appl. No.: 14/599,641

(22) Filed: Jan. 19, 2015

(65) Prior Publication Data

US 2015/0132739 A1 May 14, 2015

Related U.S. Application Data (62) Division of application No. 13/058,954, filed as application No. PCT/DK2009/050209 on Aug. 24, 2009, now Pat. No. 8,980,301.

(30) Foreign Application Priority Data

Aug. 22, 2018 (WO) ................ PCT/DK2008/000299

(51) Int. Cl.
| | | |
|---|---|---|
| *A61K 35/19* | (2015.01) | |
| *A61K 38/36* | (2006.01) | |
| *A61K 38/17* | (2006.01) | |
| *A61K 38/15* | (2006.01) | |
| *A61K 35/33* | (2015.01) | |
| *A61K 35/15* | (2015.01) | |
| *A61L 24/10* | (2006.01) | |
| *B04B 5/04* | (2006.01) | |
| *C12N 5/0787* | (2010.01) | |
| *C12N 5/078* | (2010.01) | |
| *A61L 26/00* | (2006.01) | |

(52) U.S. Cl.
CPC .............. *A61K 35/19* (2013.01); *A61K 35/15* (2013.01); *A61K 35/33* (2013.01); *A61K 38/15* (2013.01); *A61K 38/17* (2013.01); *A61K 38/36* (2013.01); *A61K 38/363* (2013.01); *A61L 24/106* (2013.01); *B04B 5/04* (2013.01); *C12N 5/0642* (2013.01); *C12N 5/0644* (2013.01); *A61L 26/0042* (2013.01); *B04B 2005/0485* (2013.01); *C12N 2501/905* (2013.01)

(58) Field of Classification Search
CPC .... A61K 2300/00; A61K 35/19; A61K 35/15; A61K 38/17; A61K 38/363; A61K 38/36; A61K 35/16; A61L 24/106; A61L 26/0042; A61L 27/3616; A61L 27/38; C12N 5/0642; C12N 5/0644; C12N 2533/56; A61M 1/3633; A61M 1/3693; A61M 1/029; A61M 1/0218; A61M 2202/0449; C12Q 1/56; G01N 33/86; G01N 2333/75; G01N 2333/974; G01N 33/49; G01N 33/491; B01L 2300/0681; B01L 2400/0409; B01L 3/50215; B01D 21/262; B04B 5/04; B04B 2005/0485; A61B 5/150755; C07K 14/75; Y10T 436/25

See application file for complete search history.

(56) References Cited

U.S. PATENT DOCUMENTS

| | | | |
|---|---|---|---|
| 3,814,248 A | * | 6/1974 | Lawhead ............ B01L 3/50215 |
| | | | 210/117 |
| 5,733,545 A | | 3/1998 | Hood, III |
| 8,168,230 B2 | | 5/2012 | Evangelista |
| 8,980,301 B2 | | 3/2015 | Lundquist et al. |
| 2004/0217046 A1 | | 11/2004 | Konrad |
| 2005/0023182 A1 | | 2/2005 | Shah |
| 2006/0140923 A1 | | 6/2006 | Evangelista |
| 2008/0089867 A1 | | 4/2008 | Fernandes et al. |
| 2008/0199513 A1 | | 8/2008 | Bertta et al. |

FOREIGN PATENT DOCUMENTS

| | | | | |
|---|---|---|---|---|
| EP | 1 637 145 A1 | 3/2006 | | |
| JP | 6-197887 A | 7/1994 | | |
| JP | H08165245 A | 6/1996 | | |
| JP | 2001508807 A | 7/2001 | | |
| JP | 2004521938 A | 7/2004 | | |
| WO | WO-0132289 A1 | * 5/2001 | ............. | A61K 35/14 |
| WO | 02/081007 A1 | 10/2002 | | |
| WO | WO-02081007 A2 | * 10/2002 | ............. | A61M 1/36 |
| WO | 2004103440 A1 | 12/2004 | | |

OTHER PUBLICATIONS

ThermoFisher. Blood fractionation protocol for collection of white blood cells. Thermo Fisher Scientific. 2002;1-5.*
Laurens et al. Fibrin structure and wound healing. J Thromb Haemost. 2006;4:932-939.*
Convert. Convert between times gravity ('g) and centrifuge rotor speed (RPM). Thermo Fisher Scientific. 2005;1-3.*
Jay et al., "How Anticoagulants Work", Techniques in Regional Anesthesia and Pain Management, 10, 2006, pp. 30-39.
Diss et al., "Osteotome Sinus Floor Elevation Using Choukroun's Platelet-Rich Fibrin as Grafting Material: A 1-Year Prospective Pilot Study with Microthreaded Implants", 2008, Oral Surg Med Oral Pathol Oral Radio Endod, vol. 105, Mosby, Inc., pp. 572-579.

(Continued)

*Primary Examiner* — Lynn Y Fan
(74) *Attorney, Agent, or Firm* — Ohlandt, Greeley, Ruggiero & Perle, L.L.P.

(57) ABSTRACT

A blood product (10), a method for preparing the blood product, a blood product obtainable by the method and a blood product preparing container means. The blood product comprises components from whole blood, especially fibrin, thrombocytes and leukocytes. The blood product (10) comprises a first layer (21), a second layer (22) and a third layer (23). The second layer (22) is adjacent to the first layer (21) and the third layer (23). The first layer (21) defines a first outer surface (24) of the blood product (10) and the third layer (23) defining a second outer surface (25) of the blood product (10). The first layer (21) comprises a majority of fibrin, the second layer (22) comprises a majority of thrombocytes and the third layer (23) comprises a majority of leukocytes.

19 Claims, 5 Drawing Sheets (56) References Cited

OTHER PUBLICATIONS

Dohan, David M. et al., "Platelet-rich fibrin (PRF): A second-generation platelet concentrate. Part I: Technological concepts and evolution", Oral Surg Oral Med Oral Pathol Oral Radiol Endod, 2006, pp. E37-E44, vol. 101, No. 3.
Dohan, David M. et al., "Platelet-rich fibrin (PRF): A second-generation platelet concentrate. Part II: Platelet-related biologic features", Oral Surg Oral Med Oral Pathol Oral Radiol Endod, 2006, pp. E45-E50, vol. 101, No. 3.
Dohan, David M. et al., "Platelet-rich fibrin (PRF): A second-generation platelet concentrate. Part III: Leucocyte activation: A new feature for platelet concentrates?", Oral Surg Oral Med Oral Pathol Oral Radiol Endod, 2006, pp. E51-E55, vol. 101, No. 3.
Choukroun, Joseph et al., "Platelet-rich fibrin (PRF): A second-generation platelet concentrate. Part IV: Clinical effects on tissue healing", Oral Surg Oral Med Oral Pathol Oral Radiol Endod, 2006, pp. E56-E60, vol. 101, No. 3.
Choukroun, Joseph et al., "Platelet-rich fibrin (PRF): A second-generation platelet concentrate. Part V: Histologic evaluations of PRF effects on bone allograft maturation in sinus lift", Oral Surg Oral Med Oral Pathol Oral Radiol Endod, 2006, pp. 299-303, vol. 101, No. 3.
Sutton, Don W. et al., "Cell Separation in the Buffy Coat", Biorheology, 1988, pp. 663-673, vol. 25, No. 4.
Kalus, M. et al., "Human Buffy Coat in Three-Dimensional Matrix Tissue Cultures and Monolayers", Pathologia et Microbiologia, 1968, pp. 353-364, vol. 31, No. 6.
Everts, P. A. M. et al., "Differences in platelet growth factor release and leucocyte kinetics during autologous platelet gel formation", Transfusion Medicine, 2006, pp. 363-368, vol. 16, No. 5.
Raja V, Sunitha et al., "Platelet-rich fibrin: Evolution of a second-generation platelet concentrate", Indian J Dent Res, 2008, pp. 42-46, vol. 19, No. 1.
Diss, Antoine et al., "Osteotome sinus floor elevation using Choukroun's platelet-rich fibrin as grafting material: a 1-year prospective pilot study with microthreaded implants", Oral Surg Oral Med Oral Pathol Oral Radiol Endod, 2008, pp. 572-579, vol. 105, No. 5.
International Search Report for International Application No. PCT/DK2009/050209, dated Oct. 6, 2009, seven (7) pages.
Dohan-Ehrenfest et al., "Three-Dimensional Architecture and Cell Composition of a Choukroun's Platelet-Rich Fibrin Clot and Membrane", J. Periodontology 81: 546-555 (2010).
Hattori:"A Simple Micromethod of Preparing Peripheral Leukocytes and Platelets for Electron Microscopy", Arch. Histol. Jap. 32 (4) : 307-313 (1970).
Nunes et al, "Micro-Buffy Coas of Whole Blood: A Method for the Electron Microscopic Study of Mononuclear Cells", Stain Technology 54 (5): 257-260 (1979).
Lundquist et al., "Bioactivity and Stability of Endogenous Fibrogenic Factors in Platelet-Rich Fibrin", Wound Repair and Regeneration 16: 356-363, May 1, 2008.
Oral Surg. Oral Med. Oral Pathol. Oral Radiol. Endod., 2006, vol. 101, No. 3, pp. 51-55.
Thermo Fisher Scientific Inc., "Convert between times gravity (xg) and centrifuge rotor speed (RPM)", Thermo Scientific, Tech Tip #40, TR0040.1, 1 page, 2009.
Brazilian Office Action dated Jun. 3, 2019 from corresponding Brazilian Patent Application No. PI0918402-3 dated Jun. 3, 2019, 36 pages.
Balbino et al.; "Mechanisms Involved in Healing: a Review", Brazilian Journal of Pharmaceutical Sciences, vol. 41, No. 1, Jan./Mar. 2005, 46 pages.

\* cited by examiner

MULTILAYERED BLOOD PRODUCT

This is a Divisional Application of U.S. patent application Ser. No. 13/058,954, filed Feb. 14, 2011, an application filed as a national stage under 371 of Application No. PCT/DK2009/050209 filed Aug. 24, 2009, the content of each of which is hereby incorporated by reference in its entirety.

TECHNICAL FIELD

The present invention relates to a multilayered blood product, a method for preparing the blood product, a blood product obtainable by the method and a blood product preparing container means.

BACKGROUND ART

The human coagulation system is able to stop bleeding and initiate healing. The function of the system is well known and extensively investigated. However, the importance of coagulation products in the initiation of healing has only been recognized recently.

Blood products, such as fibrin sealants and platelets concentrates, are produced by isolating the platelet rich plasma (PRP) from anti-coagulated whole blood. The presence of platelets and plasma partly imitates the natural human coagulation system upon thrombin activation. This leads to a platelet containing autologous concentrate of growth promoting factors in a fibrin matrix. Such a composition can be used for covering wound surfaces and is claimed to initiate healing.

"Platelet-rich fibrin (PRF): A second-generation platelet concentrate. Part I: Technological concepts and evolution, Oral Surg Oral Med Oral Pathol Oral Radiol Endod 2006; 101:E37-44" by David M. Dohan et al describes how to prepare a platelet rich solid fibrin network from whole blood without adding any additives or reagents. The PRF protocol is: A blood sample is taken without anticoagulant in 10-mL glass tubes or glass coated plastic which are immediately centrifuged at approximately 400 g for 10 minutes. The absence of anticoagulant implies the activation in a few minutes of most platelets of the blood sample in contact with the glass tube walls and the release of the coagulation cascades. Fibrinogen is initially concentrated in the top part of the tube, before the circulating thrombin transforms it into fibrin. A fibrin clot is then obtained in the middle of the tube, extending from the upper part of the red corpuscles at the bottom of the tube to the acellular plasma at the top. Platelets are trapped massively in the fibrin meshes. The success of this technique entirely depends on the speed of blood collection and transfer to the centrifuge. Indeed, without anticoagulant, the blood samples start to coagulate almost immediately upon contact with the tube glass, and it takes a minimum of a few minutes of centrifugation to concentrate fibrinogen in the middle and upper part of the tube. Quick handling is the only way to obtain a clinically usable PRF clot. If the duration required to collect blood and launch centrifugation is overly long, failure will occur: The fibrin will polymerize in a diffuse way in the tube and only a small blood clot without consistency will be obtained. In conclusion, the PRF protocol makes it possible to collect a fibrin clot charged with serum and platelets. By removing the clot from the tube, manually cutting of the red cells part, and manually driving out the fluids trapped in the fibrin matrix (serum), practitioners will obtain autologous fibrin membranes.

However this fibrin network includes a red thrombus containing a substantial part of red blood cells, which have to be manually cut off. Furthermore the components of the produced fibrin network, such as fibrin, leukocytes and thrombocytes, are arbitrary distributed and enmeshed within the product. The recovery of leukocytes are not described and at the low g force used, the recovery of leukocytes is low as some will be located in the red cell part. The enmeshment of cells within the fibrin leads to absent or slow release of these cells and thereby inhibits the contact-dependent antimicrobicidal potential of the included leucocytes.

"Oral Surg Oral Med Oral Pathol Oral Radiol Endod 2006; 101:E37-44 and 2006; 101:E45-50" by Dohan et al describes a network that does not represent a platelet concentrate in a shape and structure, which is directly applicable for covering wound surfaces. To obtain a shape and form/rigidity useable for covering wound surfaces and prevent red blood cell inclusion, the known platelet rich solid fibrin network will have to be reshaped manually and compressed. Furthermore, the method comprises several steps and cannot be prepared in one closed system and is therefore not convenient for clinical use.

"Cell separation in the buffy coat. Biorheology. 1988; 25(4):663-73" by Sutton et al describes how anti-coagulated full blood will separate into several layers upon centrifugation or passive sedimentation; Red blood cells, leukocytes and platelets (=buffycoat) and plasma. Further, by using centrifugation force of 10000 g for 10 minutes and using a float of density of 1.053, the buffy coat can be fixed by Glutaraldehyde, and removed for investigation; however, this cannot be used clinically due to the toxicity of the Glutaraldehyde. Several methods for extracting the buffycoat from anti-coagulated blood exists including the use of density defined substances (ie. Lymphoprep). In addition to the need for anti-coagulated blood the extracted cells will be suspended—and mixed (disorganized)—in the plasma that inevitably will be included.

EP 1637145A describes a method of filtration of cells from a suspension (eg. blood cells including platelets and leukocytes) through a sheet like porous membrane, leaving the cells in the membrane as described. The sheet porous material can be prepared from fibrin. However, no layered structure is obtained, the cell are trapped in depth in the porous material and the use of allogeneic fibrin raises the risk of cross infection from other humans. Furthermore, the method comprises several steps and cannot be prepared in one closed system and is therefore not convenient for clinical use.

Known methods are limited in their use, especially clinical use. The addition of anticoagulants prior to cell separation lead to products not completely autologous, furthermore the release of substances promoting wound healing (e.g. growth factors) requires mixing with other non-autologous substances (e.g. thrombin, $Ca_2^+$ etc.) leading to homogenous final products without the desired distribution of cells.

Known methods excluding anti-coagulation lead to a disorganized distribution of cells, the cells are locked inside the product, effectively limiting the release and potential of these cells. Furthermore these methods need manual handling outside a closed system to obtain a product physically suitable for clinical use, an inadequately defined handling that leads to a variable outcome with a lower than optimal cell yield. Furthermore, the manual handling will require labor time (cost) and prolong the preparation time.

Methods describing a well defined layered structure depend on anti-coagulation and addition of toxic components, not suitable for clinical use, for the fixation and self-sustainability of the structure obtained.

DISCLOSURE OF INVENTION

The object of the invention is to provide a new and improved blood product which overcomes or ameliorates at least one of the disadvantages of the prior art or which provides a useful alternative. The object of the invention is furthermore to provide a new and improved method for obtaining the blood product which overcomes or ameliorates at least one of the disadvantages of the prior art or which provides a useful alternative.

The object of the invention is obtained by a blood product comprising components from whole blood, especially fibrin, thrombocytes and leukocytes, the blood product comprising a first layer, a second layer and a third layer, the second layer being adjacent to the first layer and the third layer, the first layer defining a first outer surface of the blood product and the third layer defining a second outer surface of the blood product, the first layer comprising a majority of fibrin, the second layer comprising a majority of thrombocytes and the third layer comprising a majority of leukocytes. Hereby, a blood product with a multilayered structure is provided, each layer provides different functionality due to different composition of each of the layers. The blood product is self-supporting, compact and solid, and the blood product has a structure, such that the blood product is directly applicable for the intended use. By majority is meant, that a component, such as fibrin, thrombocytes or leukocytes, comprises at least 50%, 55%, 60%, 65%, 70%, 75%, 80%, 85%, 90%, 95%, 98%, 99% or even 100%, or any interval that can be defined from combinations of these mentioned percentages, volume and/or mass wise of the respective layer and/or volume- and/or mass wise of the blood product. The first, the second and the third layer are each continuous and/or substantially parallel to each other, e.g. forming a stratified and/or multilayered blood product. The blood product preferably consists of three layers, e.g. a first layer comprising a majority of fibrin, a second layer comprising a majority of thombocytes and a third layer comprising a majority of leukocytes. The blood product has preferably a maximum width/thickness-ratio of 1, 2, 3, 4 or 5, however the ratio may be up to 10, 15, 20, 25, 30, 40, 50, 60, 70, 80, 90 or even up to 100, where the width is measured along the layers of the blood product and the thickness is measured perpendicular to the layers of the blood product.

In another aspect of the invention, the blood product solely consists of components from whole blood. Hereby, a blood product is provided that solely consists of components from whole blood, meaning that no additives are added to the whole blood and/or the blood product, and that the blood product is directly derivable from whole blood, fractions of whole blood or combinations of fractions of whole blood.

In another aspect of the invention, the blood product is autologous.

In another aspect of the invention, the blood product is flexible. Hereby, a blood product is provided that can withstand applied stress during normal use without rupturing. Due to the flexibility of the blood product, the blood product conforms most continuous contours whereto the blood product is applied.

In another aspect of the invention, the blood product further comprises a first substance chosen from a group comprising fibroblasts, keratinocyte cells and hyaluronic acid. Hereby, a blood product is provided which includes additional cells known to be important for skin regeneration and thereby further improves the healing potential of chronic wounds, especially wounds in areas with low or unviable adjacent tissue. Hyaluronic acid, a known component of skin, has the potential to increase the water binding capacity of the blood product as well as increase the potential for incorporation/infiltration of the blood product in areas of tissue loss.

The invention also relates to, a blood product for therapeutic use and/or use of a blood product according to the aforementioned for therapeutic use.

The invention also relates to use of a blood product for manufacturing of a medicament for therapeutic use.

The invention also relates to a blood product for treatment of a wound and/or use of a blood product according to the aforementioned for treatment of a wound.

The invention also relates to use of a blood product for manufacturing of a medicament for treatment of a wound. Hereby, a blood product is provided which is particular suitable for manufacturing of a medicament for treatment of a wound. By applying the second outer surface defined by the third layer against the wound, the wound is kept and/or maintained substantially sterile, e.g. free of infection, as the third layer comprises a majority of leukocytes, which are the first active cells and thus controls infection and attracts other cells including macrophages, while the second layer comprises a majority of thrombocytes which comprises growth promoting factors that stimulates the fibroblast cells, while the first layer of the blood product comprises a majority of fibrin, and thus the first outer surface of the blood product provides an effective protection against contamination from the surroundings; the first layer furthermore comprises growth promoting factors, which is released over time. By applying the second outer surface defined by the third layer against the wound, the wound is kept and/or maintained substantially free of infection, as the third layer comprises a majority of leukocytes which are easily released from the product. Leukocytes are cells of the immune system defending the body against infection and foreign bodies, thus they control infection and further attracts other cells including macrophages. The second layer comprises a majority of thrombocytes which comprises growth promoting factors that stimulates the cells. As the leukocytes quickly will be released from the product, the second layer will face the wound surface for optimal delivery of growth promoting substances to the wound. The first layer of the blood product comprises a majority of fibrin, and thus the first outer surface of the blood product provides an effective protection against contamination from the surroundings; the first layer furthermore comprises growth promoting factors, which is released over time.

The invention also relates to a blood product for autologous use and/or use of a blood product according to any of claims 1-7 for autologous use.

The invention also relates to use of a blood product for manufacturing of an autologous medicament.

The invention also relates to a blood product for surgical use, e.g. to seal of an area, to prevent post surgical adherence and/or use in anastomosis procedures and/or use of a blood product according to the aforementioned for surgical use.

The invention also relates to use of a blood product for manufacturing of a medicament for surgical use.

In another aspect of the invention, the blood product is for anastomosis. Use of a blood product obtainable by a method according to the aforementioned for anastomosis.

In another aspect of the invention, the blood product is used for manufacturing of a medicament for anastomosis.

The invention relates also to a method for preparing a blood product from a volume of whole blood, the method comprising the following steps: a) placing the volume of whole blood in a container means, the container means comprising a first material defining an inner surface in which the whole blood is in contact with, b) activating coagulation of the whole blood, c) separating the whole blood into erythrocytes, serum and blood product by a centrifugal force acting on the whole blood placed in the container means, whereby the whole blood separates into layers comprising erythrocytes, blood product and serum due to the differences in densities between the erythrocytes, blood product and serum, the blood product comprising fibrin, leukocytes and thrombocytes, the applied centrifugal force being at least 1000 times greater than the gravity force, e.g. g, acting on the whole blood, the centrifugal force varying inversely with the time of the centrifugation, and d) removing the blood product from the container means. Hereby, a method is provided whereby a blood product is derivable from whole blood. The method can be processed in one cycle in a closed system, since there is no need for an isolation of the erythrocytes; however the method can also be performed using an isolation of the erythrocytes.

The yield of the method for extracting fibrin from the whole blood is at least above 10%, 20%, 30%, 40%, 50%, 60%, 70%, 80%, 90%, 95%, 97%, 98%, 99% or even 100%, while the yield of the method for extracting leukocytes from the whole blood is at least above 10%, 20%, 30%, 40%, 50%, 60%, 70%, 80%, 90%, 95%, 97%, 98%, 99% or even 100%, while the yield of the method for extracting thrombocytes from the whole blood is at least above 10%, 20%, 30%, 40%, 50%, 60%, 70%, 80%, 90%, 95%, 97%, 98%, 99% or even 100%. The obtainable blood product has a volume less than 30%, 20%, 15%, 10% or even less than 5% of the volume of the whole blood. Hereby, a method is provided whereby a blood product is obtainable by e.g. centrifugation giving rise to a centrifugal force. The applied centrifugal force is at least 1000, 2000, 3000, 4000, 5000, 6000, 7000, 8000, 9000, 10000, 11000, 12000, 13000, 14000, 15000, 16000, 17000, 18000, 19000 or even 20000 times greater than the gravity force, e.g. g, acting on the whole blood, or the applied centrifugal force is within any interval that can be defined from combinations of the mentioned numbers. The centrifugal force is applied for at least 30 seconds, 40 seconds, 50 seconds, 60 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or 30 minutes, or the centrifugal force is applied within any interval that can be defined from combinations of the mentioned numbers.

In one aspect of the invention, the yield of the method for extracting fibrin from the whole blood is at least above 60%.

In one aspect of the invention, the yield of the method for extracting leukocytes from the whole blood is at least above 50%.

In one aspect of the invention, the yield of the method for extracting thrombocytes from the whole blood is at least above 60%.

In one aspect of the invention, the centrifugal force is applied for at least 30 seconds.

In one aspect of the invention, the blood product solely consists of components from whole blood. Hereby, a method is provided whereby a blood product is derivable from whole blood, thus solely consisting of components from whole blood. Thus the method is performed without adding any additives to the whole blood and/or the blood product.

In another aspect of the invention, the coagulation in step b) is activated by the first material defining the inner surface. Hereby, a method is provided in which the coagulation is initiated when the whole blood is brought in contact with the inner surface, thus it can be avoided to add any object or the like to the whole blood to initiate coagulation.

In another aspect of the invention, the coagulation in step b) is activated by exposing the whole blood to an object, such as a glass bead. Hereby, a method is provided in which the coagulation is initiated when the whole blood is brought in contact with the object added to the whole blood. Hereby, the coagulation can be initiated at a chosen point of time, which is optimal for the method.

In another aspect of the invention, the first material of the inner surface of the container means is chosen from a group comprising of polypropylene, polyethylene, polycarbonate, polyamide, acrylonitrile butadiene styrene, styrene, modified styrene, polyurethane and other polymer materials. The polymers in the mentioned group can furthermore be glass-filled. Hereby, a method is provided where a container means with an inner surface of a first material can be typical test tubes or the like made from all kinds of polymers, metal or glass. The material can also be chosen so the material property provides a minimal adhesive force/friction between the blood product and the inner surface. Polyamide and polyurethane are preferred as these materials initiates coagulation within a preferred level of activation which is higher than the level obtained using other polymers.

In another aspect of the invention, the inner surface of the container means is surface treated, e.g. coated, in order to lower friction between the blood product and the inner surface of the first material. Hereby, a method is provided where a container means with an inner surface of a first material can be typical test tubes or the like made from all kinds of polymers, metal or glass. The inner surface can be surface treated and/or coated to obtain a minimal adhesive force/friction between the blood product and the inner surface.

In another aspect of the invention, the centrifugal force is greater than an adhesive force acting between the inner surface and the blood product. Hereby, a method is provided where the centrifugal force is dominant as compared to the adhesive force, which secures a well defined layered structure of the blood product. The centrifugal force can be at least 10, 100, 1000, 5000, 10000, 20000, 50000, 100000, 1000000 or even 10000000 times greater than the adhesive force, or the centrifugal force is within any interval that can be defined from combinations of the mentioned numbers. In another aspect of the invention, the centrifugal force and centrifugation time is of such strength that the adhesive force acting between the inner surface and the fibrin is broken/released and thereby allowing the fibrin layer to be compacted/compressed. Hereby, a method is provided where the centrifugal force is dominant as compared to the adhesive force, which secures a well defined layered structure of the blood product. The centrifugal force needed to release the adhesion to the wall will depend on the fibrin density. The fibrin density will depend on several factors including coagulation activation, fibrin concentration, time, etc. The centrifugation force can be at least 10, 100, 1000, 5000, 10000, 20000, 50000, or even 100000, g, or the centrifugal force is within any interval that can be defined from combinations of the mentioned numbers.

In another aspect of the invention, the blood product adhering to the inner surface is detached from the inner surface, at least once, during step c). Hereby, a method is provided where the possible adhesion of the blood product to the inner surface can be dealt with by separating the blood product at least once during step c). The separation can be done by mechanical means such as by cutting or the like. The compacting of the fibrin can then be performed at lower g-force as the g-force does not need to release the fibrin from the wall.

In another aspect of the invention, the method further comprises a compacting step, where the blood product is compacted by a compacting means, such as a filter placed in the container means. Hereby, a method is provided where the blood product can be compacted by e.g. a filter. The filter can be placed fixed or movable in the container means and the filter can be used to isolate the blood product.

In another aspect of the invention, the method further comprises an isolation step, where the erythrocytes are isolated from the blood product during step c). Hereby, a method is provided where the erythrocytes are isolated from the serum and the blood product during the method.

In another aspect of the invention, the method further comprises a washing step where the blood product is washed, so substantially all erythrocytes and/or serum attached to the blood product are detached. Hereby, a method is provided so the blood product is substantially clean from other components, that of the blood product itself. The serum formed during the centrifugation may be used as a washing fluid.

In another aspect of the invention, the container means is a tube comprising an open end, closable by a detachable lid, and a closed end. Hereby, a method is provided where a standard test tube or the like can be used to perform the method.

In another aspect of the invention, step b) precedes step a). Hereby, the coagulation can be activated before the whole blood is placed in the container means, thus the container means does not need to comprise any coagulation activator and/or the whole blood does not need to comprise a coagulation activator when the whole blood is placed in the container means. The coagulation can as an example, be activated during blood drawing by placing glass beads in the blood drawing tubing, or choosing a tubing material that will activate blood. Thus it can be avoided to add any object or the like to the whole blood to initiate coagulation.

In another aspect of the invention, step b) occurs at least 1 minutes before step a). Hereby a method is provided where very fast handling is not necessary. Step b) can occur at least 30 seconds, 40 seconds, 50 seconds, 60 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes or even 20 minutes before step a). The level of activation of coagulation in step b) can also be controlled by the method. This allows the time between step b) and a) to be prolonged as the cell separation in step c) has to occur before fibrin levels is sufficient to inhibit cell separation.

In another aspect of the invention, step b) occurs concurrently with step c). Hereby, the coagulation can be activated at an optimum point of time for the method during step c). The coagulation can be activated/initiated by a coagulation activator integrated into the container means, and/or by using a container material that will activate the blood. The coagulator material can be an object, such as glass beads, added to the whole blood in the container means.

In another aspect of the invention, a first substance chosen from a group comprising fibroblasts, keratinocyte cells and hyaluronic acid is added to the whole blood. Hereby, a blood product is obtainable which includes additional cells known to be important for skin regeneration and thereby further improves the healing of chronic wounds, especially wounds in areas with low or unviable adjacent tissue. Hyaluronic acid, a known component of skin, has the potential to increase the water binding capacity of the blood product as well as increase the potential for incorporation/infiltration of the blood product in areas of tissue loss.

In another aspect of the invention, the compacting means, such as a filter, has a first fixed position and a second position. The filter is fixed in a position in the part of the container means containing the erythrocytes during the first part of the centrifugation where the lecucytes and thrombocytes has been separated, while the fibrin in the serum has not been compacted. Provided that the density of the filter is less than that of serum, a release of the filter will cause the filter to be transferred to the top of the tube and thereby collecting the leucocyte and thrombocyte layer and compacting the fibrin layer.

In another aspect of the invention, the compacting means, such as a filter, is fixed in the first fixed position by a deformation in the container means wall. The filter is fixed by deforming the tube wall. The filter is released by removing the deformation of the wall.

In another aspect of the invention, plasma comprising fibrin and a buffy coat comprising leukocytes and thrombocytes are used instead of whole blood. Hereby, a method is provided where whole blood excluding erythrocytes can be used, thus the blood product is directly derivable from whole blood, fractions of whole blood or combinations of fractions of whole blood.

In another aspect of the invention, the method is performed within 15 minutes. The method is performed within at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or at least 30 minutes.

In another aspect of the invention, the blood product obtained by the method is the blood product according to any of claims 1-8.

The invention also relates to a blood product obtainable by a method according to any of claims 17-41 comprising components from whole blood, especially fibrin, thrombocytes and leukocytes, the blood product comprising a first layer, a second layer and a third layer, the second layer being adjacent to the first layer and the third layer, the first layer defining a first outer surface of the blood product and the third layer defining a second outer surface of the blood product, the first layer comprising a majority of fibrin, the second layer comprising a majority of thrombocytes and the third layer comprising a majority of leukocytes. Hereby, a blood product is obtainable with a multilayered structure; where each of the layers provides different functionality due to each layers different composition. The blood product is self-supporting, compact and solid, and the blood product has a structure, such that the blood product is directly applicable for the intended use. By majority is meant, that a component, such as fibrin, thrombocytes or leukocytes, comprises at least 50%, 55%, 60%, 65%, 70%, 75%, 80%, 85%, 90%, 95%, 98%, 99% or even 100%, or any interval that can be defined from combinations of these mentioned percentages, volume- and/or mass wise of the respective layer or volume- and/or mass wise of the blood product. The first, the second and the third layer are each continuous and/or substantially parallel to each other, e.g. forming a stratified and/or multilayered blood product. The blood product preferably consists of three layers, e.g. a first layer comprising a majority of fibrin, a second layer comprising a majority of thombocytes and a third layer comprising a majority of leukocytes. The blood product has preferably a maximum width/thickness-ratio of 1, 2, 3, 4 or 5, however the ratio may be up to 10, 15, 20, 25, 30, 40, 50, 60, 70, 80, 90 or even up to 100, where the width is measured along the layers of the blood product and the thickness is measured perpendicular to the layers of the blood product.

In another aspect of the invention, a majority of the fibrin comprised in the blood product is comprised in the first layer. Hereby, a blood product is obtainable where a majority of the fibrin comprised in the entire blood product is comprised in the first layer.

In another aspect of the invention, a majority of the thrombocytes comprised in the blood product is comprised in the second layer. Hereby, a blood product is obtainable where a majority of the thrombocytes comprised in the entire blood product is comprised in the second layer.

In another aspect of the invention, a majority of the leukocytes comprised in the blood product is comprised in the third layer. Hereby, a blood product is obtainable where a majority of the leukocytes comprised in the entire blood product is comprised in the third layer.

In another aspect of the invention, the blood product solely consists of components from whole blood. Hereby, a blood product is obtainable that solely consists of components from whole blood, meaning that no additives are added to the whole blood and/or the blood product, and the blood product is directly derivable from whole blood, fractions of whole blood or combinations of fractions of whole blood.

In another aspect of the invention, the blood product is autologous.

In another aspect of the invention, the blood product is flexible. Hereby, a blood product is obtainable that can withstand applied stress during normal use without rupturing. Due to the flexibility of the blood product, the blood product conforms most continuous contours whereto the blood product is applied.

In another aspect of the invention, the blood product further comprises a first substance chosen from a group comprising fibroblasts, keratinocyte cells and hyaluronic acid. Hereby, a blood product includes additional cells known to be important for skin regeneration and thereby further improves the healing of chronic wounds, especially wounds in areas with low or unviable adjacent tissue. Hyaluronic acid, a known component of skin, has the potential to increase the water binding capacity of the blood product as well as increase the potential for incorporation/infiltration of the blood product in areas of tissue loss.

In another aspect of the invention, the blood product is for therapeutic use. Use of a blood product obtainable by a method according to the aforementioned for therapeutic use.

In another aspect of the invention, the blood product is used for manufacturing of a medicament for therapeutic use.

In another aspect of the invention, the blood product is for treatment of a wound. Use of a blood product obtainable by a method according to the aforementioned for treatment of a wound.

In another aspect of the invention, the blood product is used for manufacturing of a medicament for treatment of a wound. Hereby, a blood product is obtainable which is particular suitable for manufacturing of a medicament for treatment of a wound. By applying the second outer surface defined by the third layer against the wound, the wound is kept and/or maintained substantially sterile, e.g. free of infection, as the third layer comprises a majority of leukocytes, which are the first active cells and thus controls infection and attracts other cells including macrophages, while the second layer comprises a majority of thrombocytes which comprises growth promoting factors that stimulates wound healing and/or granulation, while the first layer of the blood product comprises a majority of fibrin, and thus the first outer surface of the blood product provides an effective protection against contamination from the surroundings; the first layer furthermore comprises growth promoting factors, which is released over time. By applying the second outer surface defined by the third layer against the wound, the wound is kept and/or maintained substantially free of infection, as the third layer comprises a majority of leukocytes which are easily released from the product. Leukocytes are cells of the immune system defending the body against infection and foreign bodies, thus they control infection and further attracts other cells including macrophages. The second layer comprises a majority of thrombocytes which comprises growth promoting factors that stimulates the cells. As the leukocytes quickly will be released from the product, the second layer will face the wound surface for optimal delivery of growth promoting substances to the wound. The first layer of the blood product comprises a majority of fibrin, and thus the first outer surface of the blood product provides an effective protection against contamination from the surroundings; the first layer furthermore comprises growth promoting factors, which is released over time.

In another aspect of the invention, the blood product is used for autologous use. Use of a blood product obtainable by a method according to the aforementioned for autologous use.

In another aspect of the invention, the blood product is used for manufacturing of an autologous medicament.

The invention also relates to a blood product for surgical use, e.g. to seal of an area, to prevent post surgical adherence and/or use in anastomosis procedures and/or use of a blood product according to the aforementioned for surgical use.

In another aspect of the invention, the blood product is for anastomosis. Use of a blood product obtainable by a method according to the aforementioned for anastomosis.

In another aspect of the invention, the blood product is used for manufacturing of a medicament for anastomosis.

The invention also relates to a blood product preparing container means for preparing a blood product according to any of claims 1-8, wherein the blood product preparing container means comprises polyamide and/or polyurethane. Hereby, a blood product preparing container means is provided which activates the coagulation of whole blood, or more specific provides a complement activation, and at the same time comprises a polymer material, which is preferred over glass containers, due to the polymers fragility and/or costs, and other polymere containers due to their coagulation-inactive properties. The fact that polyamide and/or polyurethane activates the coagulation of whole blood is surprising and provides a better alternative to the typical known glass container means and coagulation-inactive polymere container means, as the blood product preparing container means combines the advantages of the known glass container means and polymere container means.

The invention also relates to use of a blood product preparing container means according to claim 58 for manufacturing of a blood product according to any of claims 1-8.

The invention also relates to a blood product preparing container means, wherein the blood product preparing container means comprises polyamide and/or polyurethane. Hereby, a blood product preparing container means is provided which activates the coagulation of whole blood, or more specific provides a complement activation, and at the same time comprises a polymer material, which is preferred over glass containers, due to the polymers fragility and/or costs, and other polymere containers due to their coagulation-inactive properties. The fact that polyamide and/or polyurethane activates the coagulation of whole blood is surprising and provides a better alternative to the typical known glass container means and coagulation-inactive polymere container means, as the blood product preparing container means combines the advantages of the known glass container means and polymere container means.

The invention also relates to use of a blood product preparing container means according to claim 60 for manufacturing of a blood product.

BRIEF DESCRIPTION OF THE DRAWING

The invention is explained in detail below with reference to the drawing, in which.

DETAILED DESCRIPTION

FIGS. 1 to 4 illustrates respectively a first, second, third and fourth embodiment of a container means 1. The container means 1 in the four embodiments comprises a cavity having an inner surface 3. The cavity being defined by a wall 4, a closed end 12 and an open end closeable by a lid 2. The container means 1 defines a volume of whole blood 5 and is closed to the surroundings via the lid 2 mounted on the open end of the container means 1. The container means 1 can be made of any material, and the material can be chosen, so that the material of the container means 1 due to contact with the whole blood 5 via the inner surface 3 activates the coagulation cascade of the whole blood 5, which is the case for the first embodiment in FIG. 1 and the third embodiment in FIG. 3. Alternatively, the material of the container means 1 can be chosen so that the material is inactive in relation to the whole bloods 5 coagulation cascade, which is the case for the second embodiment in FIG. 2 and the fourth embodiment in FIG. 3, where an object 7, made of a material that activates the bloods 5 coagulation cascade, instead is added to the whole blood 5, such that the object 7 is used to activate the whole bloods 5 coagulation cascade. The inner surface 3 of the container means 1 in the four embodiments can be coated and/or surface treated in order to lower the friction between the inner surface 3 and any components of the blood 5. Furthermore the material of the container means 1 can be chosen, so that a low friction between the inner surface 3 and any component of the blood 5 is obtained, e.g. by choosing a material with a low protein binding capacity. In the third and fourth embodiment shown in FIGS. 3 and 4 a compaction means 8, such as a filter, is placed in the container means 1, whereby the blood product 10 is compacted against the compaction means.

Figure 1:
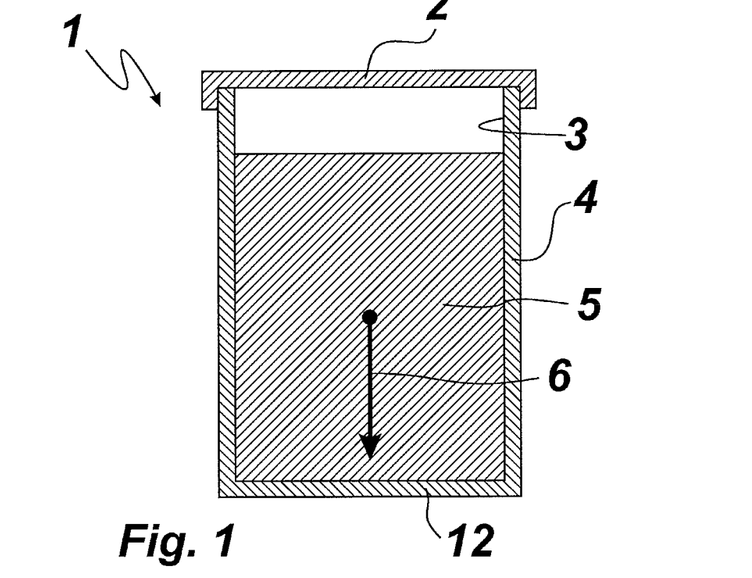
FIG. 1 shows a cross sectional view of a first embodiment of the container means according to the invention.
Figure 2:
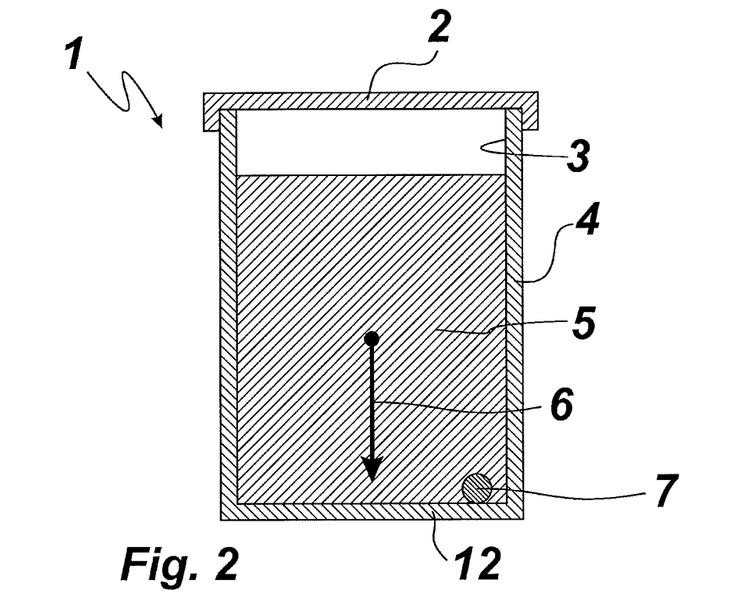
FIG. 2 shows a cross sectional view of a second embodiment of the container means according to the invention.
Figure 3:
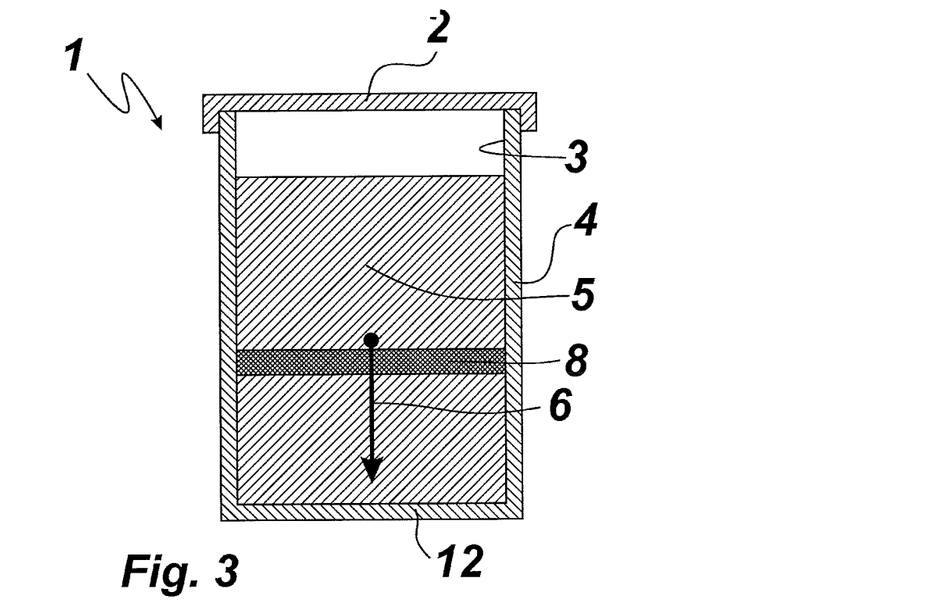
FIG. 3 shows a cross sectional view of a third embodiment of the container means according to the invention.
Figure 4:
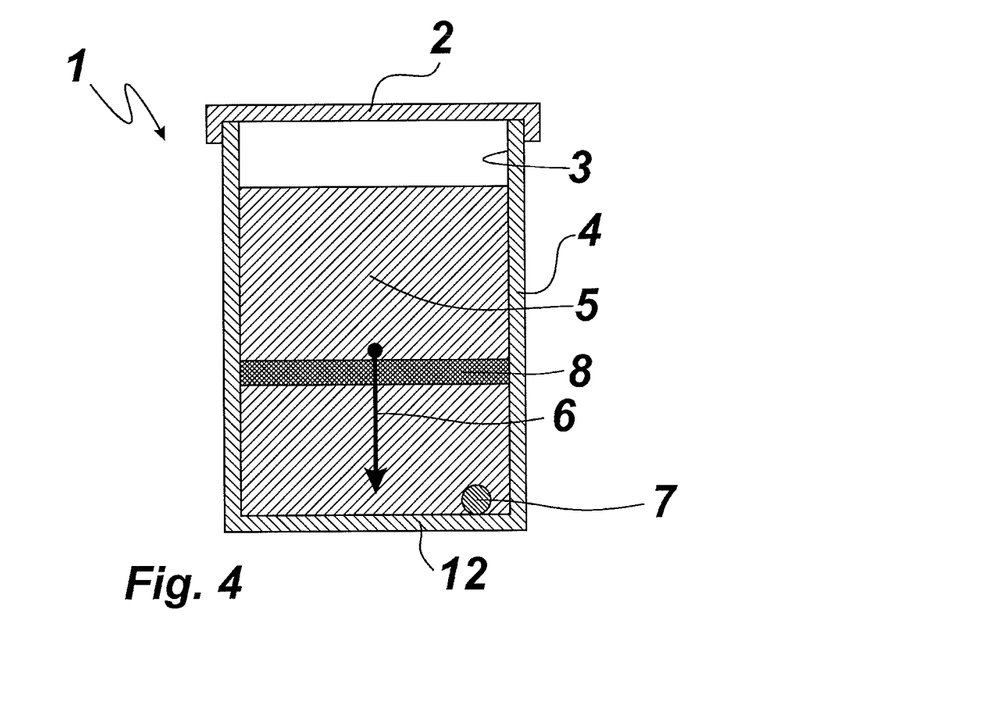
FIG. 4 shows a cross sectional view of a fourth embodiment of the container means according to the invention.
Figure 5:
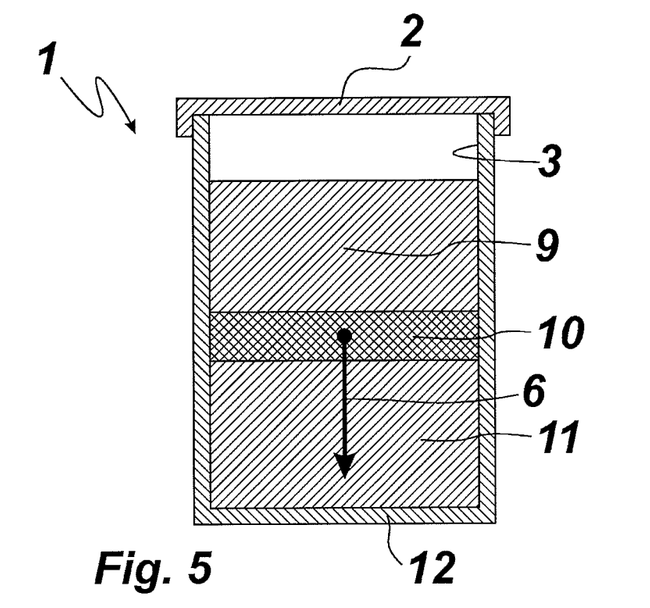
FIG. 5 shows a cross sectional view of the first embodiment of the container means according to the invention.
Figure 6:
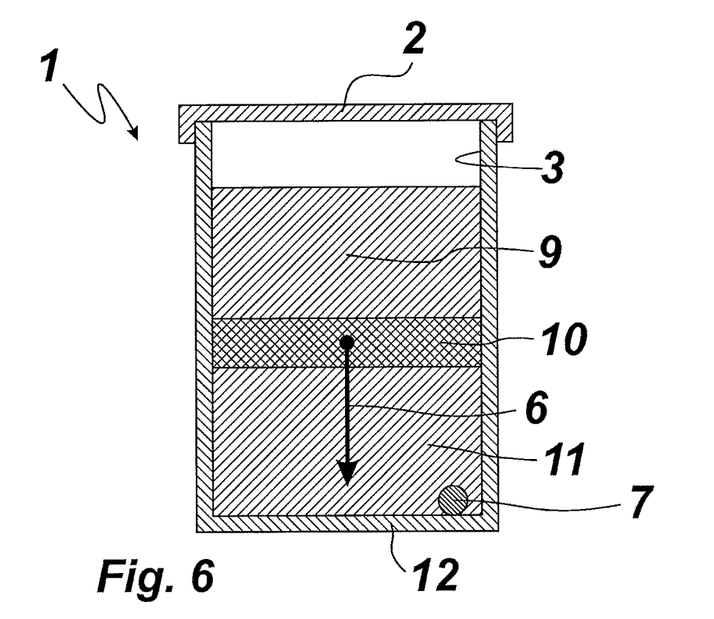
FIG. 6 shows a cross sectional view of the second embodiment of the container means according to the invention.
Figure 7:
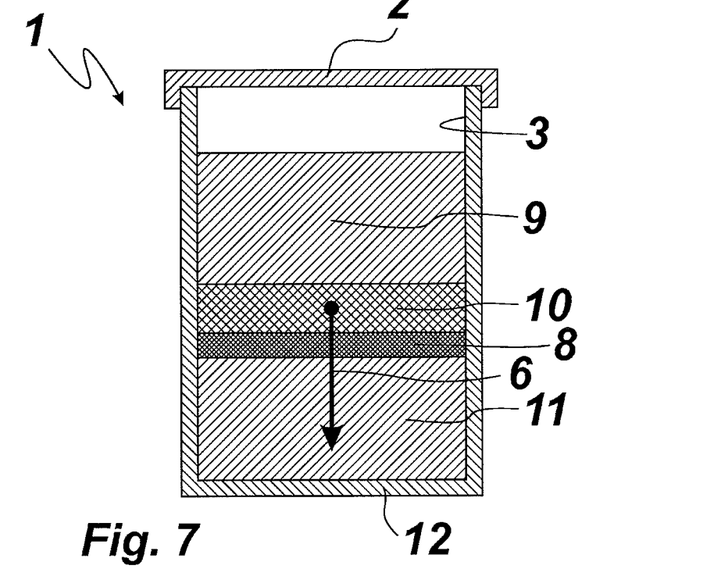
FIG. 7 shows a cross sectional view of the third embodiment of the container means according to the invention.
Figure 8:
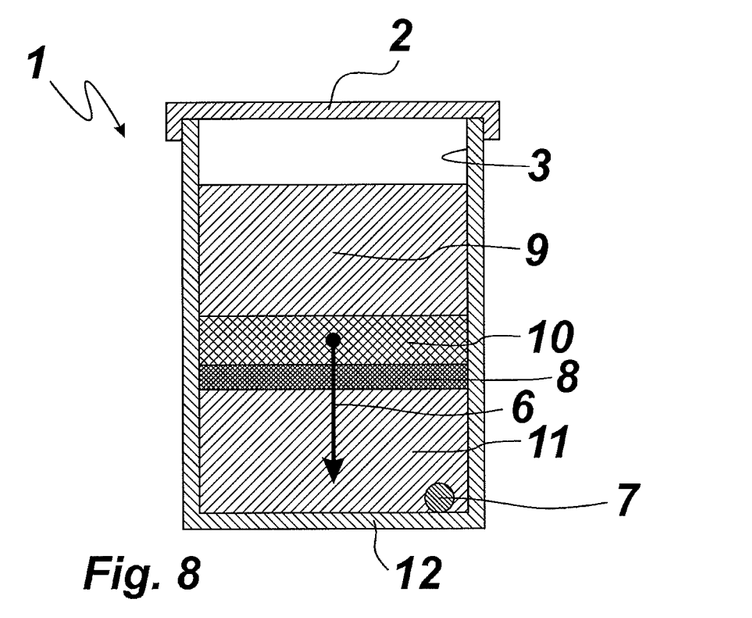
FIG. 8 shows a cross sectional view of the fourth embodiment of the container means according to the invention.

The compacting means 8 can be locked in the closed end 12 of the container means 1, where the erythrocytes are located, in the initial part of the process. At a later point in time the compacting means 8 can be released and provided that the density of the compacting means 8 is lower that the plasma, the compacting means will be forced to the top of the plasma. By removing the lid 2, the blood product 10 can be removed from the container means 1. The compaction means 8, or part of the compacting means, can be used to support the blood product 10 during transport from the container means 1.

The whole blood 5 in all four embodiments are subjected to a centrifugal force 6 acting downwards as illustrated, however the centrifugal force 6 is not limited to act in the shown direction. The centrifugal force 6 functions as a separation means, since the components of the whole blood 5 have different densities and thus will respond differently to the centrifugal force 6.

FIGS. 1 to 4 illustrates the four embodiments of the container means 1 at a point of time where the centrifugal force 6 just been applied, hence no separation of the whole blood 5 is visible, while FIGS. 5 to 8 respectively shows the first, second, third and fourth embodiment of the container means 1 at a point of time where the centrifugal force 6 has been acting sufficiently long and with sufficiently magnitude, hence the whole blood 5 has separated into serum 9, with the fibrin distributed through this serum part, platelets and leucocytes layer 10 and erythrocytes 11. At a later point in time the compacting means 8 can be released and provided that the density of the compacting means 8 is lower than that of the serum, the compacting means will be forced to the top of the serum and thereby releasing the fibrin from the wall and compacting the fibrin. By removing the lid 2, the blood product 10 can be removed from the container means 1. The compaction means 8, or part of the compacting means, can be used to support the blood product 10 during transport from the container means 1.

Figure 9:
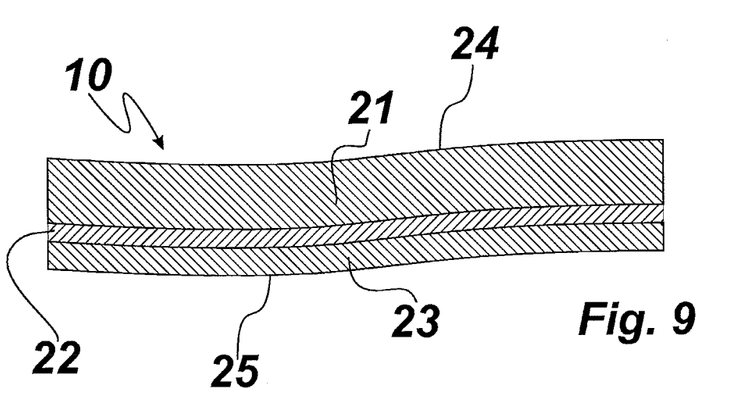
FIG. 9 illustrates a cross sectional view of an embodiment of the blood product according to the invention.

FIG. 9 illustrates a schematic cross sectional view of the blood product 10 comprising a first layer 21, a second layer 22 and a third layer 23, where the second layer is adjacent to the first layer 21 and the third layer 23. The first layer 21 defines a first outer surface 24 of the blood product 10 and the third layer 23 defines a second outer surface of the blood product 10. The first layer 21 comprises a majority of fibrin, while the second layer 22 comprises a majority of thrombocytes and the third layer 23 comprises a majority of leukocytes. Thus the blood product 10 has a well defined multilayer structure with each layer having different compositions and therefore having different functionalities.

Figure 10:
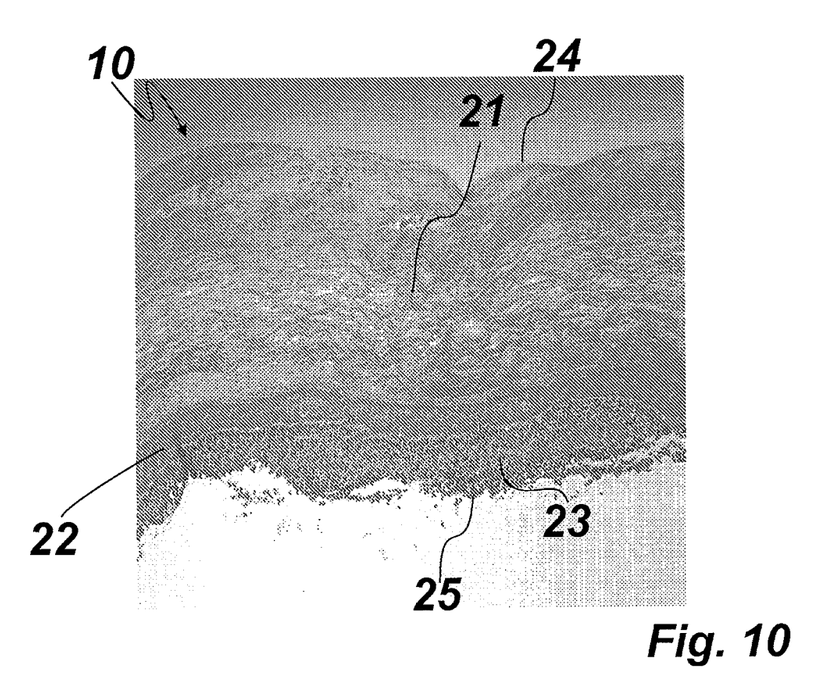
FIG. 10 shows a cross sectional view of an embodiment of the blood product according to the invention.

FIG. 10 shows a cross sectional view of a blood product obtained experimentally by using a test tube made of polypropylene as container means.

The invention has been described with reference to a preferred embodiment. However, the scope of the invention is not limited to the illustrated embodiment, and alterations, combinations and modifications can be carried out without deviating from the scope of the invention.

EXAMPLES

Example 1

1. Take a plastic container (eg. a 2 ml microcentrifuge tube) and add a coagulation trigger, eg. 4 glass beads (diameter 2 mm)
2. Draw blood into the plastic container.
3. Mix the blood and coagulation activator end-over-end for 2 min.
4. Spin the container at 16200 g for 20 min.
5. After this the blood product will be formed in a layer between the red blood cells and the serum.
6. Remove the blood product using forceps.

In this method the needed spin time and spin speed will depend on the power of activation. E.g. if the coagulation activation is high, the cells must be separated before they are trapped in the fibrin network, this will require a high spin speed. Due to the high spin speed, spin time can be low.

Example 2

1. Take a standard 50 ml centrifugation tube container and ad a coagulation trigger, eg. glass beads.
2. Draw blood into the centrifugation tube.
3. Mix the blood in the tube for 1 min.
4. Spin the tube at 3000 g for 20 min
5. Open the lid and loosen the fibrin (formed in the serum in the top part) from the wall (using a thin plastic stick or needle)
6. Spin the sample another 5 min at 3000 g.
7. After this the blood product will be formed in a layer between the red cell and serum.
8. Remove the blood product using forceps

Example 3

1. Take a 20 ml container (inner diameter: 26 mm) prepared out of polyamide or polyurethane
2. Ad a lid and create a vacuum inside the container
3. Insert a needle in the patient
4. Connect the needle to the container without losing the vacuum
5. Draw blood into the plastic container by the help of the vacuum.
6. Spin the tube at 15000 g for 12 min
7. After this the blood product will be formed in a layer between the red cell and serum.
8. Remove lid and remove the blood product with for forceps

Example 4

1. Take a 20 ml container (inner diameter: 26 mm) prepared out of polyamide or polyurethane
2. Place a disk in the bottom of the container. The density of the disk shall be less than 1, preferable as low as possible.
3. Fixate the disk in the bottom of the container, eg by compressing the wall of the container.
4. Ad a lid and create a vacuum inside the container
5. Insert needle in the patient
6. Connect the needle to the container without losing the vacuum
7. Draw blood into a plastic container by the help of the vacuum.
8. Spin the tube at 3000 g for 8 min. At this stage the leucocytes will be on top of the red blood cells and the fibrin will be polymerized through the upper serum layer as the g force is low and not able to compress it on top of the platelets.
9. Release the disk in the bottom
10. Spin the tube at 3000 g for 2 min. This will cause the disk to move to the top and thereby collecting the leukocytes and platelets and compress the fibrin layer into one sheet.
11. Remove lid and remove the blood product, that is placed in top of the contain

Example 5

1. Take a 20 ml container (inner diameter: 26 mm) prepared out of polyamide or polyurethane
2. Place a disk in the bottom of the container. The density of the disk shall be less than 1, preferable as low as possible.
3. Fixate the disk in the bottom of the container, eg by compressing the wall of the container.
4. Create a vacuum inside the container and ad a lid
5. Insert a needle in the patient
6. Connect the needle to the container without losing the vacuum
7. Draw blood into a plastic container by the help of the vacuum.
8. Spin the tube at 3700 g for 3 min. At this stage the leucocytes will be on top of the red cells and the fibrin will be polymerized through the upper serum layer as the g force is low and not able to compress it on top of the platelets.
9. Wait for 8 minutes.
10. Release the disk in the bottom
11. Spin the tube at 3000 g for 2 min. This will cause the disk to move to the top and thereby collecting the leukocytes and platelets and compress the fibrin layer into one sheet.
12. Remove lid and remove the blood product, that is placed in top of the container As it appear from the above examples, the combination of coagulation activation, spin speed (g), spin time, rest time between spin can be varied within some limits.

These are illustrated on below tables:

| Coagulation activation | Spin speed | 1. Spin time | Coagulation time after or during 1 spin | 2. Spin |
|---|---|---|---|---|
| Low | Low | Long | Long | Yes, high |
| Low | Low | Long | Long | Yes, can be low if fibrin adhesion to container wall is mechanical released from wall or adhesion to the wall is low. |
| Low | High | Short | Long | Yes, high |
| High | High | Long | Short | No |
| High | High | Short | Short | Yes, high |

If processing with a disk:

| Coagulation activation | Spin speed | 1. Spin time | Coagulation time after or during 1 spin | 2. Spin were the disk is released | |
|---|---|---|---|---|---|
| Low | Low | Long | Long | Low | |
| Low | High | Short | Long | Low | |
| High | High | Long | Short | Low | |
| High | High | Short | Short | Low | |

Example 6

Optimization of Relative Centrifugation Force and Time

1. Full blood was drawn into 6 ml EDTA tubes (Vacutainer, BD®).
2. 20 ml container (inner diameter: 26 mm) prepared out of polyamide or polyurethane were filled with 18 ml and spun at different RCFs for different times
3. Samples (~300 µl) were taken by a syringe at the bottom (approx 5 mm above the bottom) and top (approx 5 mm below the surface) after the above spin times—afterwards the spin was continued to obtain the next sample. Bottom samples were diluted 1:1 with D-PBS.
4. Samples were analyzed by automated cell counting (XE 2100, Sysmex Corporation) and cell numbers in the original sample calculated. Results are given in millions of cells per ml.

Millions of platelets per milliliter in the upper (top) and lower (bottom) part of blood centrifuged at the given relative centrifugation force (g) as a function of time (min):

|  | Minutes | | | | | |
|---|---|---|---|---|---|---|
|  | 0 | 1 | 3 | 5 | 7 | 11 |
| 2000 g top | 178 | 480 | 224 | 113 | 59 | 13 |
| 2000 g bottom | 178 | 7 | 5 | 3 | 2 | 4 |
| 3000 g top | 178 | 378 | 103 | 38 | 14 | 0 |
| 3000 g bottom | 178 | 3 | 2 | 5 | 3 | 1 |
| 3700 g top | 178 | 364 | 97 | 27 | 8 | 0 |
| 3700 g bottom | 178 | 2 | 11 | 2 | 1 | 0 |

Millions of Leucocytes per milliliter in the upper (top) and lower (bottom) part of blood centrifuged at the given relative centrifugation force (xg) as a function of time (min):

|  | Minutes | | | | | |
|---|---|---|---|---|---|---|
|  | 0 | 1 | 3 | 5 | 7 | 11 |
| 2000 g top | 7.43 | 0.28 | 0 | 0 | 0 | 0 |
| 2000 g bottom | 7.43 | 0.89 | 0.02 | 0.13 | 0.26 | 0.12 |
| 3000 g top | 7.43 | 0.19 | 0 | 0 | 0.01 | 0 |
| 3000 g bottom | 7.43 | 0.07 | 0.04 | 0.11 | 0.02 | 0.02 |
| 3700 xg top | 7.43 | 0.05 | 0.03 | 0 | 0 | 0 |
| 3700 xg bottom | 7.43 | 0.03 | 0.59 | 0.07 | 0.02 | 0.01 |

Example 7

Growth Factor Release as a Response to Chronic Wound Fluid

1. The blood product was generated by the method given in example 1.
2. The blood products was cut in half and placed in 100 µl PBS1% BSA or 100 µl chronic wound fluid (collected over 24 hrs from a venous leg ulcer) and incubated at 37 degrees celcius.
3. After given time points (1, 2, 3.5, 7, 14, 22 and 29 hours) the samples were spun at 16000 g for 10 min, and the supernatant transferred to a new tube, added ¹⁄₁₀th (81 µl sample+9 µl PI) Protease Inhibitor (Complete®, Roche) and frozen at −80 degree celcius.
4. Platelet derived growth factor—AB levels in were determined by using an ELISA kit (DuoSet® ELISA cat. No. DY222, R&D systems) as described by the manufacturer. PDGF-AB concentrations in the original samples were calculated.

Platelet derived growth factor AB (PDGF-AB) release from blood product (ng/ml blood product) as a function of time (hrs).

|  | Time (hours) | | | | | |
|---|---|---|---|---|---|---|
|  | 1 | 2 | 4 | 7 | 22 | 29 |
| Chronic Wound fluid (control) | 0 | 0 | 0 | 0 | 0 | 0 |
| Blood product in PBS | 153 | 172 | 160 | 174 | 206 | 233 |
| Blood product in chronic wound fluid | 426 | 490 | 602 | 497 | 234 | 275 |

Example 8

1. The blood product was generated by the method given in example 1.
2. Two blood products were incubated in 1 ml DMEM (PAA, Germany) at 37 C and 5% CO2 for 48 hrs.
3. In parallel 2 blood products were incubated in 1 ml DMEM (PAA, Germany) including lipopolysaccharide ((10 ng/ml) (LPS derived from *Escherichia coli*; L2654; Sigma-Aldrich) at 37 C and 5% CO2 for 48 hrs.
4. After 48 hrs the media were transferred to microcentrifuge tubes and spun 20 min at 16200×g. The supernatants were frozen at −80 C until analysis.
5. Proteome profiler Arrays ARY007 and ARY005 (both R&D systems) were performed as described by R&D systems, except that buffer 4 (ARY007) were used in both kits. 420 ul supernatant were diluted in 500 ul buffer 4 and 580 ul buffer 5 as described by R&D systems.
6. Reactivity with arrays were detected using chemiluminescent HRP substrate (Immobilon Western™, Millipore, US).
7. Light emission were captured using a Fluorchem 3000 system (Alpha Innotech, US). Mean pixel density were extracted by the Flourchem software (Alpha Innotech, US).

| Substance detected | Blood product (Mean pixel density) | Blood product + Lipopolysaccharide (Mean pixel density) |
|---|---|---|
| CXCL8 (IL-8) | 2605 | 404 |
| CXCL10 (IP-10) | 305.5 | 48.5 |
| MMP-8 | 518 | 214 |
| IL-1ra | 1825.5 | 1117.5 |
| IL-16 | 171 | 105 |
| MMP-9 | 2663.5 | 1729.5 |
| Angiopoietin-1 | 676.5 | 537.5 |
| PDGF-AB/PDGF-BB | 851.5 | 704.5 |

-continued

| Substance detected | Blood product (Mean pixel density) | Blood product + Lipopolysaccharide (Mean pixel density) |
|---|---|---|
| PDGF-AA | 1357 | 1159.5 |
| CXCL16 | 300 | 256.5 |
| TIMP-1 | 2507.5 | 2170.5 |
| Endostatin | 187 | 175.5 |
| Angiogenin | 689 | 650.5 |
| MIF | 1989 | 1880.5 |
| IGFBP-2 | 1942 | 1883.5 |
| IGFBP-3 | 444 | 468 |
| EGF | 612.5 | 670.5 |
| IGFBP-1 | 291.5 | 401 |
| sICAM-1 | 635.5 | 894.5 |
| PAI-1 | 1940 | 2897.5 |
| CCL5 (RANTES) | 4104 | 6151.5 |
| CD26 | 458.5 | 828.5 |
| VEGF | 246.5 | 891.5 |
| CXCL1 (GRO-alpha) | 336 | 2236 |
| CCL4 (MIP-1-beta) | 7 | 117.5 |
| CCL2 (MCP-1) | 6.5 | 334 |
| G-CSF | 7.5 | 429.5 |
| IL-1Beta | 7 | 600 |
| IL-6 | 8 | 2094.5 |

The invention claimed is:

1. A method for preparing a blood product for application to a wound from a volume of whole blood, the method comprising the following steps:
   placing the volume of whole blood in a container, the container comprising a first material defining an inner surface which contacts the whole blood;
   separating the whole blood into (1) erythrocytes, (2) a blood product comprising fibrin, thrombocytes, and leukocytes, and (3) serum by using an applied centrifugal force that is at least 1000 times greater than gravity to act on the whole blood,
   wherein the applied centrifugal force is applied for a time that is sufficient to separate the blood product into three layers of (a) the fibrin, (b) the leukocytes, and (c) the thrombocytes;
   activating coagulation of the whole blood; and
   removing the blood product from the container as a single, three-layered product.

2. The method according to claim 1, wherein the coagulation is activated by the first material defining the inner surface and the first material is a material that activates coagulation.

3. The method according to claim 1, wherein the first material of the inner surface of the container is selected from the group consisting of: polypropylene, polyethylene, polycarbonate, polyamide, acrylonitrile butadiene styrene, styrene, modified styrene, and polyurethane.

4. The method according to claim 1, wherein the inner surface of the container comprises a surface coating that lowers friction between the three-layered blood product and the container.

5. The method according to claim 1, wherein the centrifugal force is greater than an adhesive force acting between the inner surface and the three-layered blood product.

6. The method according to claim 1, wherein the three-layered blood product adhering to the inner surface is detached from the inner surface, at least once, during the activating coagulation.

7. The method according to claim 1, wherein the method further comprises compacting the three-layered blood product with a compactor, and wherein the compactor is a filter placed in the container.

8. The method according to claim 1, wherein the method further comprises isolating the erythrocytes from the three-layered blood product during the activating coagulation.

9. The method according to claim 1, wherein the method further comprises a washing step where the three-layered blood product is washed so that if present, substantially all erythrocytes and serum attached to the three-layered blood product are detached.

10. The method according to claim 1, wherein a first substance selected from the group consisting of: fibroblasts, keratinocyte cells, and hyaluronic acid is added to the whole blood.

11. The method according to claim 7, wherein the compactor has a first fixed position and a second position relative to the container.

12. The method according to claim 11, wherein the container comprises a deformable wall to maintain the compactor in the first fixed position.

13. The method according to claim 1, wherein the separating occurs concurrent with the activating coagulation.

14. The method according to claim 1, wherein the three-layered blood product comprises in substantially parallel layers: fibrin in a majority by volume of a first layer, thrombocytes in a majority by volume of a second layer and leukocytes in a majority by volume of a third layer.

15. The method according to claim 1, wherein the blood product is configured for application to the wound so that the third layer is in direct contact with the wound.

16. The method according to claim 15, wherein the third layer comprises leukocytes in a majority by volume of the third layer.

17. The method according to claim 15, wherein whole blood is obtained from a patient having the wound so that the blood product is autologous.

18. The method according to claim 1, wherein the first material of the inner surface of the container is polyamide or polyurethane.

19. The method according to claim 1, wherein the removing is performed with forceps.

* * * * *